(12) United States Patent
Moriyama

(10) Patent No.: US 6,679,835 B2
(45) Date of Patent: Jan. 20, 2004

(54) ENDOSCOPE DEVICE

(75) Inventor: Hiroki Moriyama, Akishima (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 09/892,134

(22) Filed: Jun. 26, 2001

(65) Prior Publication Data

US 2002/0013510 A1 Jan. 31, 2002

(30) Foreign Application Priority Data

Jun. 30, 2000 (JP) .......................... 2000-199743

(51) Int. Cl.$^7$ .................................................. A61B 1/00
(52) U.S. Cl. ....................................... 600/133; 600/132
(58) Field of Search .................................. 600/133, 132

(56) References Cited

U.S. PATENT DOCUMENTS 4,067,776 A * 1/1978 Khan ........................... 435/183
4,862,872 A * 9/1989 Yabe et al. ................... 600/133
5,749,829 A * 5/1998 Yokoi et al. ................. 600/153

FOREIGN PATENT DOCUMENTS

JP 5-285103 11/1993

OTHER PUBLICATIONS

CIRCON 1997 Complete Product Catalog, "CIRCON ACMI USA Series ACN–1 SO Flexible CystoNephroscope," p. U88.*
CIRCON ACMI 1997 Complete Product Catalog, pp. U–87 and 88 (featuring ACN–1 and ACN–1 SO Flexible Cysto-Nephroscopes).*

* cited by examiner

*Primary Examiner*—John Mulcahy
(74) *Attorney, Agent, or Firm*—Scully, Scott, Murphy & Presser

(57) ABSTRACT

The endoscope device comprises an endoscope suitable for high temperature autoclave sterilization, an endoscope not suitable for high temperature autoclave sterilization, an external endoscope device to which these endoscopes are connected, and an identification part for identifying whether the endoscope is suitable for high temperature autoclave sterilization.

17 Claims, 6 Drawing Sheets

ENDOSCOPE DEVICE

This application claims benefit of Japanese Application No. 2000-199743 filed in Japan on Jun. 30, 2000, the contents of which are incorporated by this reference.

BACKGROUND OF THE INVENTION

1. Field of the Invention

The present invention relates to an endoscope device comprising an endoscope suitable for high temperature autoclave sterilization, an endoscope not suitable for high temperature autoclave sterilization, and an external device connected to these endoscopes.

2. Description of the Related Art

Endoscopes and some treatment instruments used in the medical field are inserted into the body. To again use an endoscope or such a treatment instrument already used once for another patient, the endoscope and the treatment instrument must be cleaned and disinfected after inspection and treatment is over so that infection between patients via the endoscope and the treatment instrument is prevented.

Recently, autoclave sterilization is becoming the standard disinfection and sterilization processing of a medical instrument. This is because this sterilization method does not involve a complicated operation, allows using the equipment immediately after sterilization, and requires low running cost.

Japanese Patent Laid-Open No. H5-285103, for example, discloses an autoclave sterilizer for an endoscope which autoclaves the endoscope without affecting the functions of the endoscope.

The environment of the above mentioned autoclave sterilization presents very severe conditions for an endoscope, which is a precision electronic equipment having such an image pick-up device as a CCD. Therefore an endoscope to be autoclaved has resistance to severe conditions by taking various countermeasures, to include high pressure, high temperature and steam countermeasures, compared with an endoscope intended to be used for general disinfection and sterilization.

In other words, if an endoscope which is not suitable for autoclave sterilization is sterilized using a high temperature autoclave sterilizer by mistake, the endoscope may fail immediately or soon thereafter.

If the user has an endoscope device comprising an endoscope suitable for autoclave sterilization, an endoscope not suitable for autoclave sterilization, and an external endoscope device where these endoscopes can be connected, such as a light source device and a video processor, the endoscope not suitable for autoclave sterilization may be autoclaved by mistake during disinfection and sterilization.

SUMMARY OF THE INVENTION

It is an object of the present invention to provide an endoscope device where autoclaving an endoscope not suitable for autoclave sterilization by mistake is prevented.

Since the endoscope device according to the present invention comprises an endoscope suitable for high temperature autoclave sterilization, an endoscope not suitable for high temperature autoclave sterilization, an external endoscope device where these endoscopes are connected, and an identification part which identifies whether the endoscope is suitable for high temperature autoclave sterilization, failure due to high temperature autoclaving of the endoscope not suitable for high temperature autoclave sterilization can be prevented.

The above and other objects, features and advantages of the invention will become more apparent from the following description when taken in conjunction with the accompanying drawings.

BRIEF DESCRIPTION OF THE DRAWINGS

FIG. 1 is a diagram depicting an endoscope device comprising an endoscope suitable for high temperature autoclave sterilization and an external endoscope device, and FIG. 2 is a diagram depicting a configuration example of the endoscope device where an endoscope suitable for high temperature autoclave sterilization and an endoscope not suitable for high temperature autoclave sterilization are combined;

FIG. 3A is a diagram depicting an endoscope suitable for autoclave sterilization having a plate on which characters are written, and FIG. 3B is a diagram depicting a reusable treatment instrument suitable for autoclave sterilization having a plate on which characters are written;

FIG. 7A is a diagram depicting the endoscope connector part of the endoscope suitable for high temperature autoclave sterilization and a water-proof cap which is attached to the endoscope connector part, and FIG. 7B is a diagram depicting the configuration when the water-proof cap for high temperature autoclave sterilization is connected to a housing case for sterilization;

FIG. 9A is a diagram depicting a configuration of the endoscope device, and FIG. 9B is a diagram depicting a display example on the display screen of a monitor.

DESCRIPTION OF THE PREFERRED EMBODIMENTS

The embodiments of the present invention will now be described referring to the accompanying drawings.

The first embodiment of the present invention will be described referring to FIG. 1 and FIG. 2.

Figure 1:
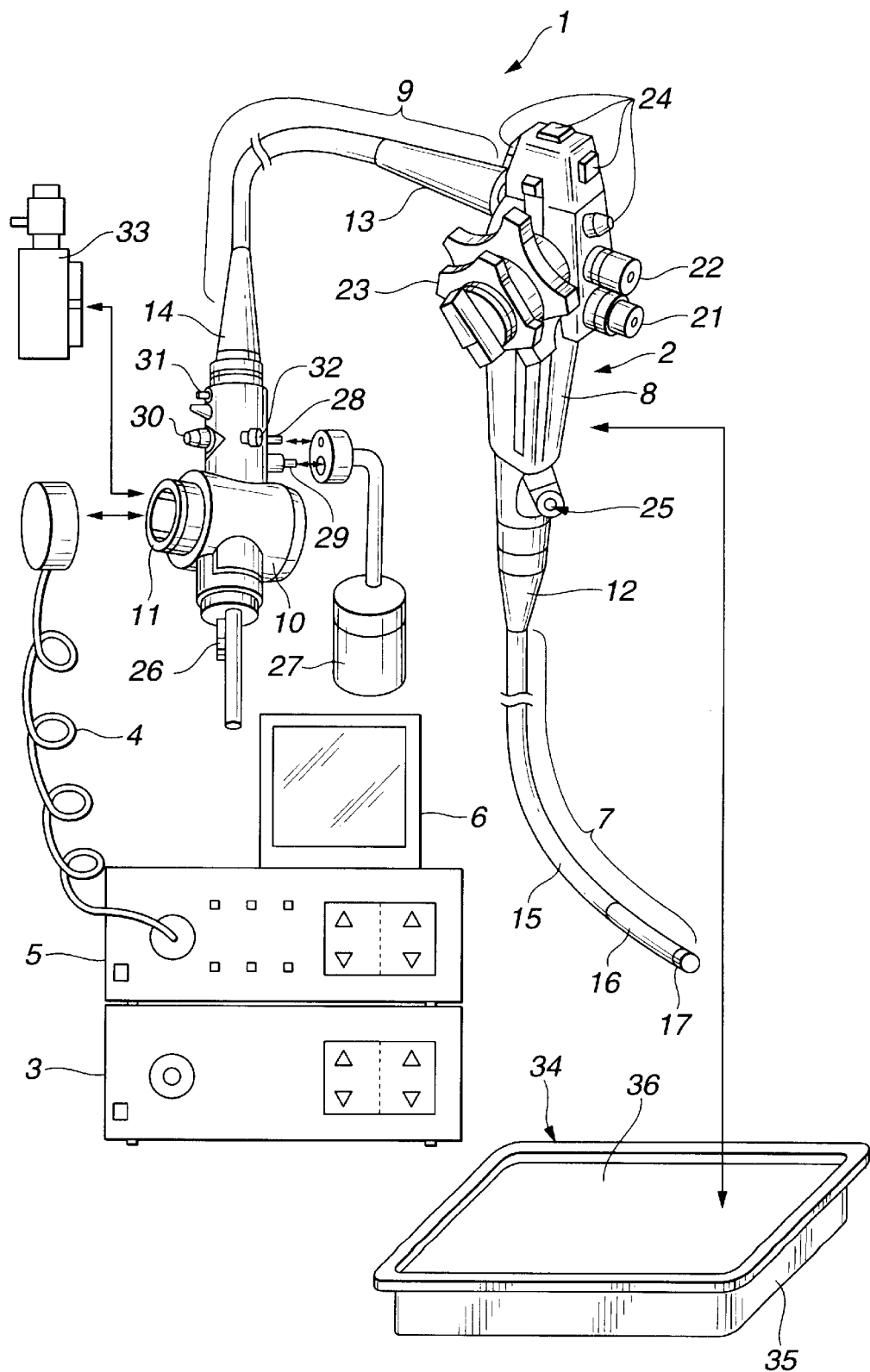
FIG. 1 and FIG. 2 are diagrams depicting the first embodiment, where

FIG. 1 shows the endoscope 2 which is an electronic endoscope having an image pick-up means (not shown) which is autoclaved (also called high temperature autoclave sterilization) after the endoscope used for observation or treatment is cleaned. This endoscope 2, along with such external endoscope devices as light source device 3, video processor 5 and monitor 6, constitute the endoscope device 1.

The light source device 3 is attachably and detachably connected to/from the endoscope 2 freely, and supplies illumination light to the light guide (not shown) disposed in the endoscope 2. The video processor 5 is connected to the endoscope 2 via the signal cable 4 and controls the image pick-up means, processes signals obtained from the image pick-up means, and outputs standard video signals to the monitor 6. The monitor 6, where image signals from the video processor 5 are input, display the endoscope images.

The endoscope 2 comprises an elongated flexible insertion part 7, an operation part 8 disposed at the base of the insertion part 7, and a flexible universal cord 9 extended from the side of the operation part 8.

At the end of the universal cord 9, there is an endoscope connector part 10 which is attachably and detachably connected to/from the light source device 3 freely. On the side of the endoscope connector part 10, there is an electric connector part 11 where a signal cable 4 to be connected to the video processor 5 is attachably and detachably connected freely. At this electric connector part 11, there is a vent hole (not shown) connecting the inside and the outside of the endoscope 2. To this electric connector part 11, the waterproof cap 33 with a pressure regulating valve can be attachably and detachably connected freely. And in this water-proof cap 33, there is a pressure regulating valve (not shown).

At a connection part between the insertion part 7 and the operation part 8, an insertion part bending prevention element 12, comprised of an elastic element, is disposed for preventing sharp bending at this connection part. At a connection part between the operation part 8 and the universal cord 9, an operation part bending prevention element 13, having a similar configuration as above, is disposed. Also at a connection part between the universal cord 9 and the endoscope connector part 10, a connector bending prevention element 14, having a similar configuration as above, is disposed.

The insertion part 7 is comprised of a flexible tube part 15, a curving part 16 and a tip part 17 which are linked in this sequence from the operation part 8 side.

The flexible tube part 15 is flexible. The curving part 16 curves, for example, vertically and horizontally by operating the curving operation knob 23 of the operation part 8. At the tip part 17, the observation optical system, the illumination optical system (not shown), etc. are disposed.

At the operation part 8, a gas supply/water supply operation button 21 for operating the gas supply or water supply, a suction operation button 22 for operating the suction operation, a curving operation knob 23, a plurality of remote switches 24 for remote-controlling the video processor 5, and a treatment instrument insertion hole 25 linked to the treatment instrument channel (not shown) are disposed. To this treatment instrument channel, the treatment instrument is inserted and also functions as a suction pipe to suck body fluid from the body.

At the tip face of the tip part 17, there is an observation window of the observation optical system, an illumination window of the illumination optical system, a liquid supply hole and a gas supply/water supply nozzle for ejecting a cleaning liquid and gas, and a suction hole which also functions as a tip opening of the treatment instrument channel (not shown).

By a gas supply operation or water supply operation, cleaning liquid or gas is ejected from the gas supply/water supply nozzle to the observation window.

At the endoscope connector part 10, a gas supply mouth piece 26, a water supply tank pressure mouth piece 28, a liquid supply mouth piece 29, a suction mouth piece 30 and an injection mouth piece 31 are disposed. The gas supply mouth piece 26 is attachably and detachably connected to/from the gas supply source freely (not shown) which is incorporated into the light source device 3. The water supply tank pressure mouth piece 28 and the liquid supply mouth piece 29 are attachably and detachably connected to/from the water supply tank 27, which is the liquid supply source freely. The suction mouth piece 30 is connected to the suction source (not shown) for sucking from the suction hole. The injection mouth piece 31 is connected to the water supply means (not shown) for supplying water from the liquid supply hole. At the endoscope connector part 10, an earth terminal mouth piece 32 for feeding high frequency leak current, which is generated to the endoscope during high frequency processing, back to the high frequency processor, is disposed.

When the endoscope 2 is autoclaved, a housing case for sterilization (hereinafter housing case) 34 is used.

The housing case 34 is comprised of a tray 35 which is a case element to house the endoscope 2 and the cover element 36. On the tray 35 and the cover element 36, a plurality of vent holes (not shown) are formed. Therefore the high pressure steam is guided into the housing case 34 via the vent holes during autoclave sterilization.

In the tray 35, a control part (not shown) corresponding to the shape of the endoscope 2 is disposed. This control part is for setting each part of the endoscope 2 to predetermined positions, and an insertion part control part for housing the flexible insertion part 7 is also disposed in this control part.

Now the typical conditions for autoclaving the endoscope 2 will be described.

The conditions are stated in the US Standard ANSI/AAMI ST37-1992, approved by the American National Standards Institute, as issued by the Association for the Advancement of Medical Instrumentation. Here the conditions are four minutes in the sterilization process at 132 C. in the case of a pre-vacuum type, or ten minutes in the sterilization process at 132 C. in the case of a gravity type.

The temperature conditions during the sterilization process of autoclave sterilization differs depending on the type of autoclave sterilizer and the time length of the sterilization process. Generally the temperature is set in a 115 C. to 138 C. range. However, some sterilizers may be set to about 142 C.

Time conditions differ depending on the temperature conditions of the sterilization process. Normally time is set in a 3 to 60 minute range. Some sterilizers may be set to about 100 minutes.

The pressure inside the sterilization chamber in this sterilization process is normally set to about +0.2 MPa with respect to the atmospheric temperature.

Now the autoclave sterilization process of the endoscope 2 of a general pre-vacuum type will be described in brief.

At first, a water-proof cap 33 is attached to the electric connector part 11 of the endoscope 2, which is the sterilization target equipment. Then the endoscope 2 is housed in the housing case 34, and this housing case 34 is disposed in the sterilization chamber 8 (not shown). Then the pressure inside the sterilization chamber before the autoclave sterilization process is reduced (pre-vacuum process).

By the water-proof cap 33 attached to the electric connector part 11, the pressure regulating valve is closed, which closes the vent hole. In other words, the inside of the endoscope 2 is sealed water-tight from the outside.

The pre-vacuum process is for infiltrating steam into the sterilization target equipment during the sterilization process. In this process, high pressure high temperature steam spreads through the entire sterilization target equipment by reducing the pressure in the sterilization chamber. The pressure in the sterilization chamber in the pre-vacuum process is normally set to about −0.07 MPa to −0.09 MPa.

When the pressure in the sterilization chamber decreases in the pre-vacuum process, a pressure difference is generated, since the external pressure of the endoscope 2 becomes lower than the internal pressure. Then the pressure regulating valve of the water-proof cap 33 opens, and the inside and the outside of the endoscope 2 are connected via the vent hole. This prevents the pressure difference between the inside and the outside of the endoscope 2 from becoming too large. In other words, damage to the endoscope 2, due to the pressure difference, is prevented.

Now the sterilization process where high pressure high temperature steam is supplied to the sterilization chamber, and sterilization is executed will be described.

In the sterilization process, the inside of the sterilization chamber is pressurized. Then a pressure difference is generated, where the external pressure of the endoscope 2 is higher than the internal pressure. As a result, the pressure regulating valve of the water-proof cap 33 closes. Thereby, high pressure steam is blocked from passing through the vent hole, entering into the endoscope.

However, high pressure high temperature steam gradually enters into the endoscope, passing through the covering resin of the flexible tube 15, which is made of polymer material, or passing through the O ring made of fluorine rubber or silicon rubber, which is a sealing means disposed at the connection part of the endoscope 2.

At this time, pressure, which is the sum of the pressure reduced in the pre-vacuum process and the pressure pressurized in the sterilization process, is generated from the outside to the inside of the endoscope 2.

Then to dry the sterilization target equipment after sterilization, a drying (dry process) is executed by setting the inside of the sterilization chamber into a pressure reduced status again after the sterilization process ends.

In this dry process, drying the endoscope 2 in the sterilization chamber is promoted by reducing the pressure inside the sterilization chamber, in order to release steam from the sterilization chamber. The pressure in the sterilization chamber in the dry process is normally set to about −0.07 MPa to −0.09 MPa with respect to the atmospheric pressure. The above mentioned dry process is executed arbitrarily if required.

In the dry process after the sterilization process, pressure inside the sterilization chamber decreases, and a pressure difference is generated where the external pressure of the endoscope 2 is lower than the internal pressure. When this pressure difference is generated, the pressure regulating valve of the water-proof cap 33 opens roughly at the same time, and the inside and the outside of the endoscope 2 are connected via the vent hole. By this, generating a large pressure difference between the inside and the outside of the endoscope is prevented.

When the pressure reduction process ends, and the inside of the sterilization chamber is pressurized and a pressure difference, where the external pressure of the endoscope 2 is higher than the internal pressure, is generated, the pressure regulating valve of the water-proof cap 33 closes.

When all the processes of the autoclave sterilization completes, pressure for the amount reduced in the pressure reduction process is generated from the outside to the inside of the outer body part of the endoscope 2. By removing the water-proof cap 33 from the electric connector part 11, the inside and the outside of the endoscope 2 is connected via the vent hole. Thereby, the inside of the endoscope 2 becomes the atmospheric pressure, and the load, due to the pressure difference generated onto the outer body part of the endoscope 2, disappears.

Figure 2:
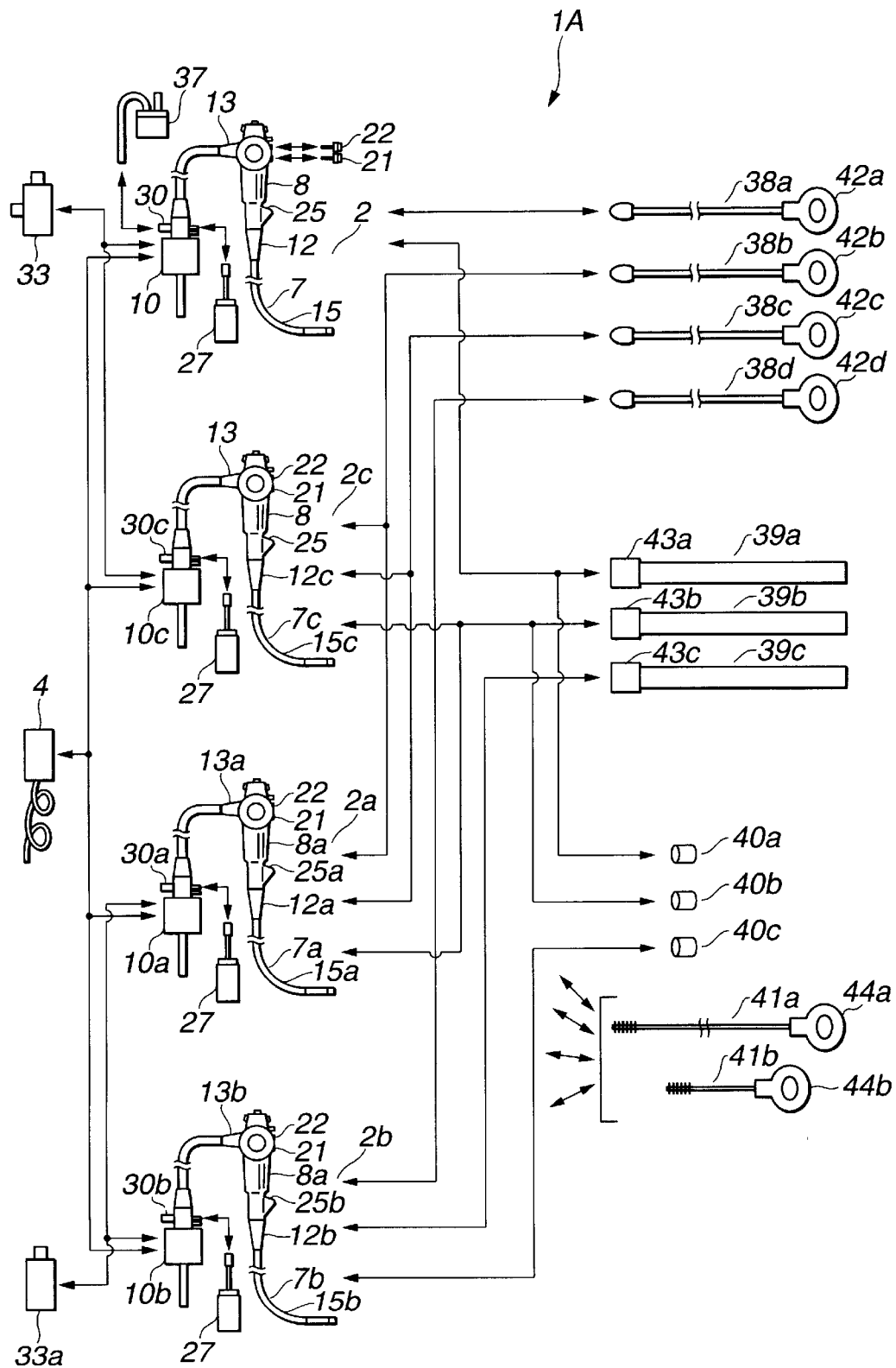

The endoscope 2 suitable for high temperature autoclave sterilization described above constitutes the endoscope device 1A along with other endoscopes, etc. as shown in FIG. 2. These endoscope include an endoscope 2c, which is suitable for high temperature autoclave sterilization just like the above mentioned endoscope 2, but has different specifications, such as insertion length, diameter and optical characteristics, or an endoscope 2a, which is not suitable for high pressure autoclave sterilization, or an endoscope 2b, which has different specifications, such as insertion length, diameter and optical characteristics, from the endoscope 2a. At this time, the light source device 3, video processor 5 and the monitor 6 are commonly used as the endoscope device.

Various other variations are possible, but now an endoscope device comprising at least one endoscope suitable for high temperature autoclave sterilization and at least one endoscope not suitable for high temperature autoclave sterilization will be described.

In this case, the signal cable 4 and the water supply tank 27 can be commonly used, and the specifications of the gas supply/water supply operation button 21 and the suction operation button 22, which are attachably and detachably to/from the operation part 8 freely, can be common. It is of course possible that the water supply tank 27, the gas supply/water supply operation button 21, and the suction operation button 22 may not be commonly used. The water supply tank 27, the gas supply/water supply operation button 21, and the suction operation button 22 support high temperature autoclave sterilization respectively.

The endoscope 2 in FIG. 2 shows the state where the attachable and detachable gas supply/water supply operation button 21 and the suction operation button 22 are removed from the operation part 8. In the endoscopes 2a, 2b and 2c, the attachable and detachable gas supply/water supply operation button 21 and the suction button 22 are attached to the operation part 8.

The numeral 37 indicates a polyp collection container. The specifications of the polyp collection container 37 is common for the suction mouth pieces 30, 30a, 30b and 30c of the endoscopes 2, 2a, 2b and 2c. And the polyp collection container 37 supports high temperature autoclave sterilization.

When the endoscopes 2, 2a, 2b and 2c are cleaned, disinfected and sterilized after endoscope inspection is over, the water-proof cap is attached to the endoscope connector parts 10, 10a, 10b and 10c instead of the signal cable 4. At this time, the water-proof cap 33 for high temperature autoclave sterilization is attached to the endoscope 2 and the endoscope 2c. And the water-proof cap 33a for disinfection and sterilization is attached to the endoscope 2a and the endoscope 2b.

During inspection, reusable treatment instruments 38a, 38b, 38c and 38d are combined with the endoscopes 2, 2a, 2b and 2c if required, as body contacting instruments. Among these, the reusable treatment instruments 38a and 38b support high temperature autoclave sterilization. The reusable treatment instruments 38c and 38d do not support high temperature autoclave sterilization.

In other words, the reusable treatment instrument 38a can be combined with the endoscope 2, but cannot be combined with the other endoscopes 2a, 2b and 2c. The reusable treatment instruments 38b and 38c can be combined with the endoscopes 2a and 2c, but cannot be combined with the other endoscopes. Also the reusable treatment instrument 38d can be combined only with the endoscope 2b.

The combination possibilities here means the combination compatibility of the inner diameter and the length of the treatment instrument channel created in each endoscope 2, 2a, 2b and 2c, and the outer diameter and the length of the reusable treatment instruments 38a, 38b, 38c and 38d.

The over tubes 39a, 39b and 39c, which are body contacting instruments, covering the insertion parts 7, 7a, 7b and 7c of each endoscope 2, 2a, 2b and 2c, are also constituting elements of the endoscope device. These over tubes 39a, 39b and 39c help the insertion of the endoscopes 2, 2a, 2b and 2c into the body. The over tubes 39a and 39b support high temperature autoclave sterilization. And the over tube 39c does not support high temperature autoclave sterilization.

The over tube 39a can be combined only with the endoscope 2. The over tube 39b can be combined with the endoscope 2a and the endoscope 2c. The over tube 39c can be combined only with the endoscope 2b.

The combination possibilities here means the combination compatibility of the outer diameter and the length of the insertion parts 7, 7a, 7b, and 7c of each endoscope 2, 2a, 2b and 2c, and the inner diameter and the length of the over tubes 39a, 39b and 39c.

Also in the present embodiment, the tip cap 40a, 40b or 40c, which are the body contacting elements, is freely attached and detached to/from the tip of the insertion part 7, 7a, 7b or 7c so as to add a new function to observation and treatment. The tip caps 40a and 40b support high temperature autoclave sterilization. The tip cap 40c does not support high temperature autoclave sterilization. And the tip cap 40a can be combined only with the endoscope 2. The tip cap 40b can be combined with the endoscope 2a and the endoscope 2c. The tip cap 40c can be combined only with the endoscope 2b.

The combination possibilities here means the combination compatibility of the outer diameter of the tip part of the insertion part 7, 7a, 7b or 7c, and the inner diameter of the tip cap 40a, 40b or 40c.

For cleaning after inspection, cleaning instruments 41a and 41b for brushing the pipes of each endoscope 2, 2a, 2b and 2c is also provided as a part of the endoscope device. These instruments 41a and 41b support high temperature autoclave sterilization, and are commonly used for each endoscope 2, 2a, 2b and 2c.

Suitable for high temperature autoclave sterilization means that the outer body and the inner structure of the endoscope and the peripheral equipment are manufactured so as to support high temperature autoclave sterilization, wherein material is changed for high voltage countermeasures, high temperature countermeasures and steam (moisture) countermeasures, or a structure is changed to smooth the finish of a surface or for withstanding high voltage, and an air tight structure to minimize the entry of steam are included in the manufacturing. Therefore the inspection performance is the same for both an endoscope which is suitable for high temperature autoclave sterilization or an endoscope which is not suitable. In terms of cost, however, the endoscope suitable for high temperature autoclave sterilization is expensive, since various technologies are included.

In this embodiment, the endoscope and peripheral instruments which are suitable for high temperature autoclave sterilization and the endoscope and peripheral instruments which are not suitable for high temperature autoclave sterilization can be identified by the color indication on the outer surface.

In other words, the general color of the endoscopes 2a and 2b which are not suitable for high temperature autoclave sterilization is black. Whereas the endoscopes 2 and 2c which are suitable for high temperature autoclave sterilization have the color pattern shown in Table 1.

TABLE 1

| Location | Color pattern | | | | |
| --- | --- | --- | --- | --- | --- |
|  | Pattern 1 | Pattern 2 | Pattern 3 | Pattern 4 | Pattern 5 |
| Appearance of flexible tube part | Black | Green | Black | Black | Green |
| Insertion part bending prevention element | Black | Black | Green | Black | Green |
| Appearance of operation part | Black | Black | Black | Green | Green |
| Operation part bending prevention element | Black | Black | Green | Black | Green |
| Appearance of connection part | Green | Green | Green | Green | Green |

In other words, as Table 1 shows, in the case of the endoscopes 2 and 2c which are suitable for high temperature autoclave sterilization, the endoscope connector parts 10 and 10c have at least green in all patterns.

In pattern 1, only the colors of the endoscope connector parts 10 and 10c are green, which is different from the endoscope 2a and the endoscope 2b.

In pattern 2, the insertion parts 7 and 7c have a different color, green, unlike the pattern 1.

In pattern 3, the bending prevention element at two locations have a different color, green, unlike the pattern 1.

In pattern 4, the operation part has a different color, green, unlike the pattern 1.

In pattern 5, green, which color is generally different from the endoscope 2a and the endoscope 2b, is used.

In other words, for the part where the color is different, the color of the entire area may be different, or the color of a part of the area may be different. The above mentioned green may be a light-yellowish green or dark green. In the pattern 4, the appearance of the operation part may be a color close to dark green, and the appearance of the connector part may be a color close to yellowish green. It is important to clearly identify the color from the black color of the endoscope 2*a* and the endoscope 2*b*.

The reusable treatment instruments 38*a* and 38*b*, over tubes 39*a* and 39*b*, tip caps 40*a*, 40*b*, and the cleaning instruments 41*a* and 41*b*, which are used with each endoscope 2, 2*a*, 2*b* or 2*c*, also have predetermined color patterns.

Specifically, in the reusable treatment instruments 38*a* and 38*b*, at least a part of the handles 42*a* and 42*b* have green color. In the reusable treatment instruments 38*c* and 38*d*, on the other hand, there is no green on the same location as the handles 42*c* and 42*d*.

In the over tubes 39*a* and 39*b*, at least a part of the grips 43*a* and 43*b* are green. Whereas in the over tube 39*c*, no green is used on a location which is the same as the grip 43*c*.

In the tip caps 40*a* and 40*b*, at least part of them is green. Whereas the tip cap 40*c* is not green.

In the cleaning instruments 41*a* and 41*b*, at least a part of the handles 44*a* and 44*b* are green.

In the polyp collection container 37 and the water supply tank 27, at least a part is green.

At least part of the water-proof cap 33 is green. Whereas the water-proof cap 33*a* has, for example, black at the same area, there is no green.

As mentioned above, in the present invention, not only each endoscope but also the peripheral instruments to be used with the endoscope can be identified by color, to indicate whether it is suitable for high temperature autoclave sterilization or whether it is not suitable for high temperature autoclave sterilization. The colors for the identification of peripheral instruments are green, even if light/dark green are different, so as to roughly match the colors for identifying an endoscope.

After an endoscope inspection is executed using the endoscope 2, 2*a*, 2*b* or 2*c* of the endoscope device with the above configuration, cleaning and disinfection or sterilization is performed. The cleaning process is the same for all endoscopes 2, 2*a*, 2*b* and 2*c*.

The endoscope 2 and the endoscope 2*c*, which are types suitable for high temperature autoclave sterilization, may be placed in the autoclave sterilizer in the disinfection or sterilization process, or may be disinfected/sterilized by chemicals. However, for the endoscope 2*a* and the endoscope 2*b*, which are not suitable for high temperature autoclave sterilization, disinfection/sterilization other than high temperature autoclave sterilization must be performed.

The general format is similar for all the endoscopes 2, 2*a*, 2*b* and 2*c*. The endoscope inspection and cleaning operations can be performed in the same way. So conventionally, there was possibility for a user to place the endoscope 2*a* or the endoscope 2*b* in an autoclave sterilizer by mistake, thinking that the endoscope 2*a* or 2*b* is suitable for high temperature autoclave sterilization. In this case, a problem soon occurs since no high pressure countermeasures, high temperature countermeasures or steam countermeasures have been taken for the endoscope 2*a* or the endoscope 2*b*.

In the present invention, an endoscope suitable for high temperature autoclave sterilization and an endoscope not suitable for high temperature autoclave sterilization are clearly identified by an indication color on the outer surface, so that placing the endoscope 2*a* or the endoscope 2*b* in an autoclave sterilizer by mistake can be prevented.

The cleaning, disinfection and sterilization operations after inspection, in particular, are often performed by a nurse or an individual other than the operator who operated the device, so clear identification is necessary for the nurse or other individual. For all the patterns, any endoscope which is not identified by green, at least on an endoscope connector part, is not suitable for high temperature autoclave sterilization.

This is because the water-proof cap 33 or the water-proof cap 33*a* is always attached to the endoscope connector part 10, 10*a*, 10*b* or 10*c* during cleaning, disinfection and sterilization. In other words, the worker can identify the color when they pay attention to the connector part when attaching the water-proof cap. And by using green for at least a part of the water-proof cap 33 with the pressure regulating valve for high temperature autoclave sterilization, the water-proof cap can be attached to the endoscope 2 or the endoscope 2*c* without fail. As a result, erroneously attaching the water-proof cap to the endoscope 2*a* or the endoscope 2*b* is prevented.

Identification is easiest if the entire color of the endoscope is green, such as in pattern 5. But it may be difficult to generate the desired green color for some material used for the outer body side. So as the other patterns show, areas to be a different color are limited. In the case of pattern 2, for example, since the flexible tube part 15 is normally longer than the operation part 8, here a worker can easily notice the color difference. The flexible tube part 15 is a part of the insertion part.

The thickness or the length of the insertion part of the endoscope differs depending on the model, which is selected depending on the purpose of the inspection and the skill of the operator. If the colors of the insertion parts 7, 7*a*, 7*b* and 7*c* are different, a user may have misunderstood that color difference is for identification based on the purpose of the inspection or the skill of the operator. The operation part 8, however, is normally the same, even if the specification of the insertion part 7 is different. So changing the color of the operation part 8, as in the case of pattern 4, makes it clear that the color identification is not for identifying a model corresponding to the purpose of inspection or the skill of the operator.

When an endoscope suitable for high temperature autoclave sterilization is colored green, for example, if instruments which can be combined with the endoscope and are suitable for high temperature autoclave sterilization are also colored green, identification is easier and the user can identify whether the instrument is suitable for high temperature autoclave sterilization.

Figure 8:
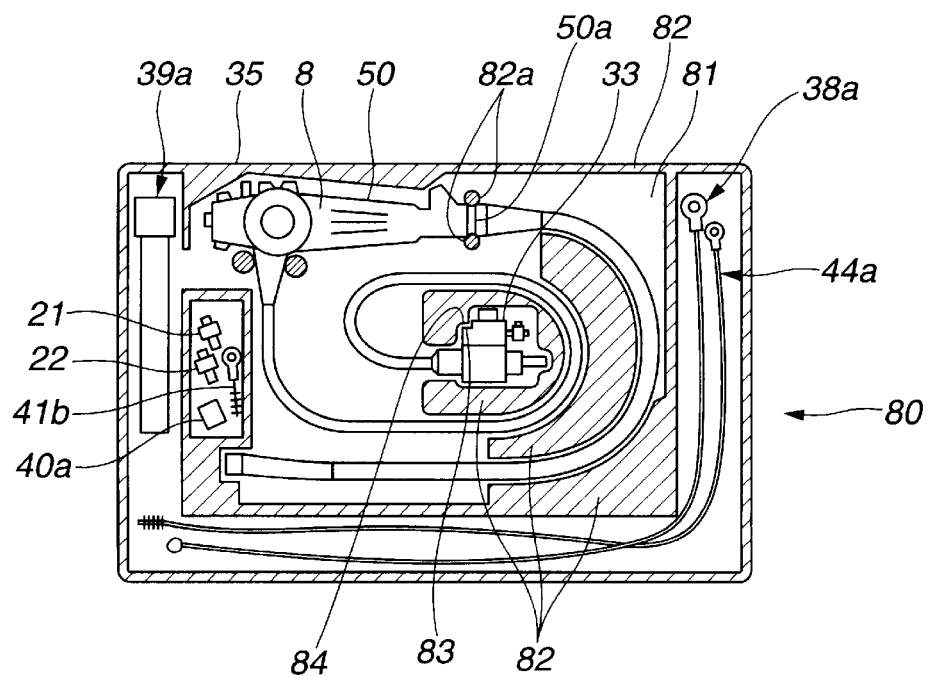
FIG. 8 is a diagram depicting the housing case for sterilization according to the sixth embodiment of the present invention.

So when an endoscope suitable for high temperature autoclave sterilization and an instrument, which can be combined with an endoscope, may contact the body fluid of a patient, and is suitable for high temperature autoclave sterilization, are used for a patient, the endoscope and the combined instrument can be autoclaved at the same time, as shown in FIG. 8.

Green color used for indication creates an image of a product which is gentle to the environment, and conveys an image of a product for high temperature autoclave sterilization which does not require chemicals for disinfection and sterilization.

It is more effective that the color identification of the endoscope 2 and the endoscope 2*c* be seen from any direction around the endoscope, compared with the case of a color which can be seen only from a specific direction. This is because the operator in charge of cleaning, disinfection and sterilization normally operates while viewing the endoscope from various directions around the endoscope. In other words, the operator rarely operates the endoscope while viewing from the top or bottom in the shaft direction, keeping the endoscope insertion part straight.

By the above mentioned configuration, the endoscope suitable for high temperature autoclave sterilization and the endoscope not suitable for high temperature autoclave sterilization can be easily identified. In other words, a recognition error can be prevented.

(Second Embodiment)

The second embodiment of the present invention will now be described referring to FIG. 3 and FIG. 4.

In the first embodiment, the endoscope suitable for high temperature autoclave sterilization and the endoscope not suitable for high temperature autoclave sterilization are identified by the difference of the indication color on the outer surface, but in this embodiment, identification is made by characters or graphics. The other configuration is the same as the first embodiment, where the same elements are denoted with the same numerals, for which description is omitted.

Figure 3A:
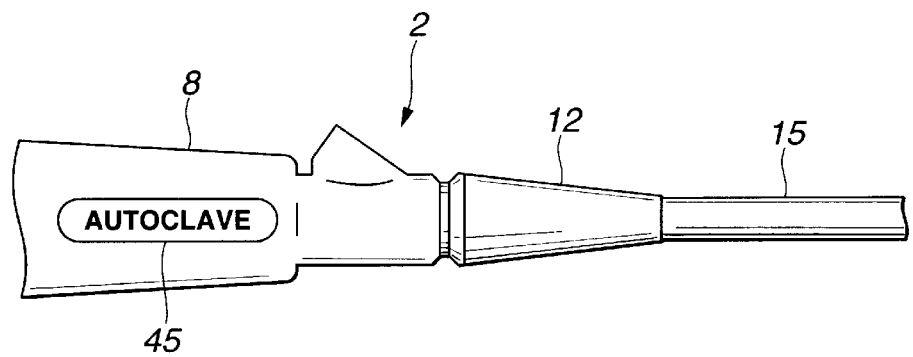
FIG. 3A and FIG. 3B are diagrams depicting the second embodiment, where

As FIG. 3A shows, in the present embodiment, a plate 45 where characters "AUTOCLAVE" are carved is attached to a part of the operation part 8 of the endoscope.

For example, when the operation part 8 of the endoscope suitable for high temperature autoclave sterilization and the endoscope not suitable for high temperature autoclave sterilization are both black, the plate 45 is green, and the characters "AUTOCLAVE" are carved in black or gold on the plate 45.

Here, in the case of the first embodiment, at least a part of the color of the operation part 8 must be changed to identify whether the endoscope is one suitable for high temperature autoclave sterilization or one not suitable for high temperature autoclave sterilization, but it may be difficult to create a desired color, depending on the material of the operation part 8.

In the present embodiment, on the other hand, a material whereby a desired color can be easily created is selected for the plate 45, and characters for identification carved on the plate makes the identification content clearer.

Figure 3B:
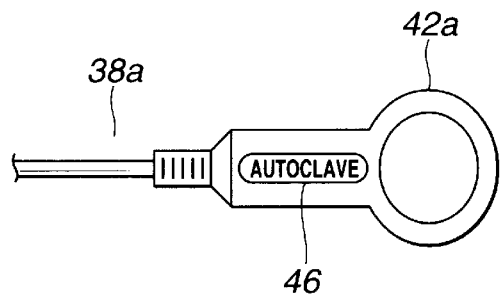

Also as FIG. 3B shows, an instrument suitable for high temperature autoclave sterilization can be easily identified by attaching a plate 46 which has a different size from the plate 45, but which has the same color and design including characters as plate 45, to the handle 42a of the reusable treatment instrument 38a.

Figure 4A:
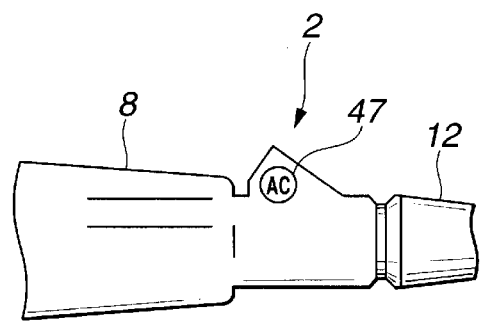
FIG. 4A is a diagram depicting an endoscope suitable for autoclave sterilization having a plate on which characters in another configuration are written.
Figure 4C:
FIG. 4C is a diagram depicting an example of a plate having a graphic, instead of characters.

Also as FIG. 4A shows, a plate 47 where abbreviated characters "AC" are written, instead of the characters "AUTOCLAVE" may be attached to a predetermined location.

Figure 4B:
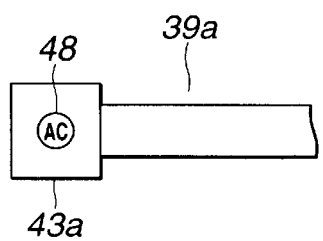
FIG. 4B is a diagram depicting an over tube suitable for autoclave sterilization having the plate shown in FIG. 4A.

Also as FIG. 4B shows, a plate 48 where characters "AC" are written, and which size is the same as or different from the plate 47, may be attached to the over tube 39a.

Abbreviated characters such as "AC" may be misunderstood for another meaning, so the plate 49, as shown in FIG. 4A, where a reference mark by a unique graphic is carved, instead of characters to indicate suitable for high temperature autoclave sterilization, may be used. This will enable a clearer identification.

As a result, a more clear identification whether the endoscope is suitable for high temperature autoclave sterilization is possible, in addition to the effect of the first embodiment.

(Third Embodiment)

The third embodiment of the present invention will now be described referring to FIG. 5.

In the first and second embodiments, whether the endoscope is suitable for high temperature autoclave sterilization is identified by color, characters or graphics, but in this embodiment, whether the endoscope is suitable for high temperature autoclave sterilization is identified by the external shape. The other configuration is the same as the above mentioned embodiments, where the same elements are denoted with the same numerals, for which description is omitted.

Figure 5:
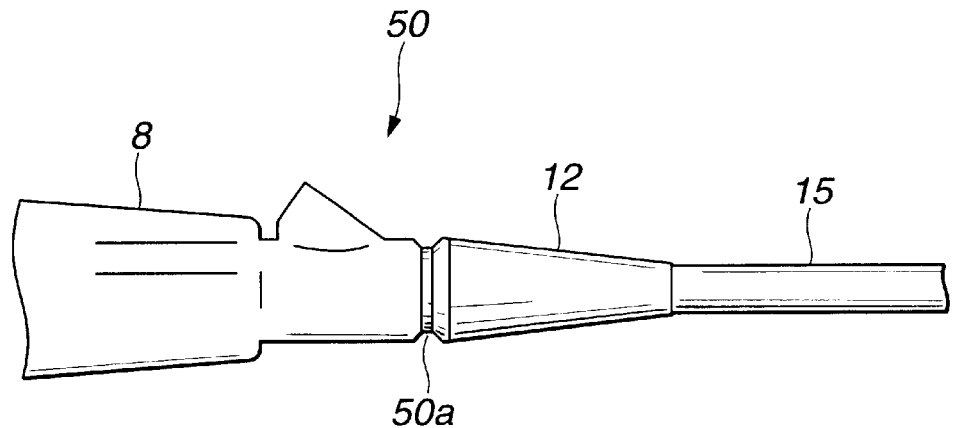
FIG. 5 is a diagram depicting a configuration of the endoscope according to the third embodiment of the present invention.

As FIG. 5 shows, in the endoscope 50 of the present embodiment, a groove part 50a in the circumference direction is created at a part of the operation part 8. Instead of a groove part, a convex part may be created for the identification part.

Since the groove or the convex part is created in the circumference direction, whether the endoscope is suitable for high temperature autoclave sterilization can be identified by seeing or touching from any direction.

Thereby, the operator-in-charge of cleaning, disinfection and sterilization can identify whether the endoscope is suitable for high temperature autoclave sterilization by external shape, even if the operator has difficulty in identifying some colors.

As a result, whether the endoscope is suitable for high temperature autoclave sterilization can be identified by touching.

(Fourth Embodiment)

The fourth embodiment of the present invention will now be described referring to FIG. 6.

In this embodiment, whether the endoscope is suitable for high temperature autoclave sterilization is identified depending on whether the attaching element required for high temperature autoclave sterilization is connected to the endoscope. The other configuration is the same as the above mentioned embodiment, where the same elements are denoted with the same numerals, for which description is omitted.

Figure 6:
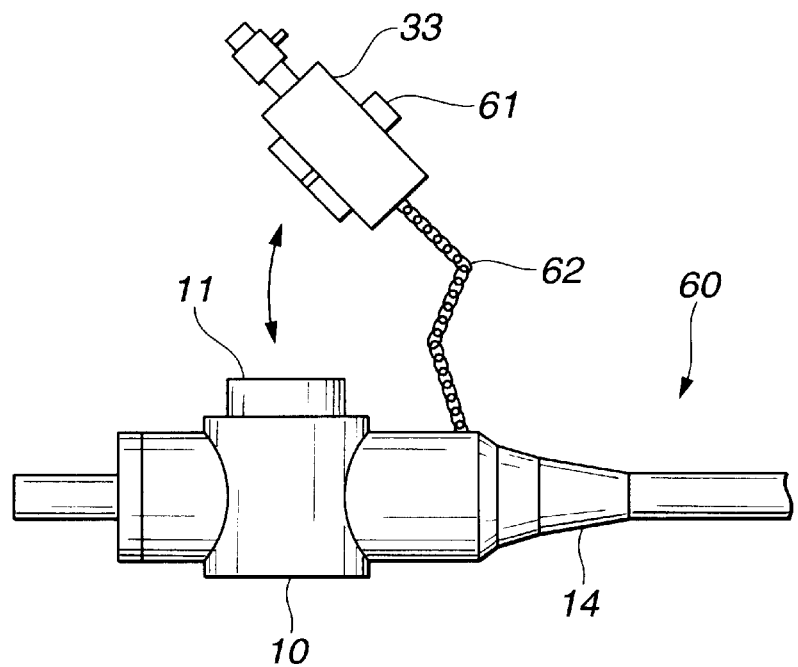
FIG. 6 is a diagram depicting a configuration of the endoscope according to the fourth embodiment of the present invention.

As FIG. 6 shows, in this embodiment, for the endoscope 60 suitable for high temperature autoclave sterilization, a water-proof cap 30 for high temperature autoclave sterilization with a pressure regulating valve 61, which is a combining element, is connected to a part of the endoscope connector part 10 via the chain 62. Thereby, the water-proof cap 33 is attached to the electric connector part 11 of the connector part 10 during the high temperature autoclave sterilization process, so that autoclave sterilization can be executed.

For the endoscope 2a and the endoscope 2b which are not suitable for high temperature autoclave sterilization, the water-proof cap 33a, which does not have a pressure regulating valve, is not connected to the endoscope connector part 10, although this is not shown.

Thereby, whether the endoscope is suitable for high temperature autoclave sterilization can be identified depending on whether the water-proof cap 33 is connected to the endoscope connector part of the endoscope. This also prevents attaching the water-proof cap 33a, which is not suitable for high temperature autoclave sterilization, to the endoscope 60 suitable for high temperature autoclave sterilization by mistake.

(Fifth Embodiment)

The fifth embodiment of the present invention will now be described referring to FIG. 7.

In the embodiment 4, whether the endoscope is suitable for high temperature autoclave sterilization is identified depending on whether the water-proof cap 33 for high temperature autoclave sterilization is connected to the endoscope connector part 10, but in the present embodiment, the water-proof cap 33, which is the attaching element for high temperature autoclave sterilization, can be attached only to the electric connector part 11 of the endoscope suitable for high temperature autoclave sterilization. The other configuration is the same as the above mentioned embodiments, where the same elements are denoted with the same numerals, for which description is omitted.

Figure 7A:
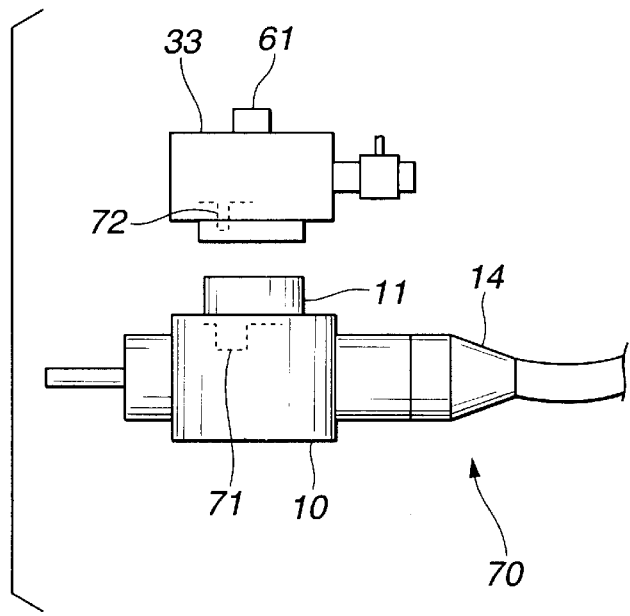
FIG. 7A and FIG. 7B are diagrams depicting the fifth embodiment of the present invention, where

As FIG. 7A shows, in this embodiment, the concave part 71 for attaching the water-proof cap 33 for high temperature autoclave sterilization is created inside the electric connector 11 of the endoscope connector part 10 of the endoscope 70 suitable for high temperature autoclave sterilization. Whereas the convex part 72 to engage with the concave part 71 inside the endoscope connector part 10 is created inside the water-proof cap 33 for the high temperature autoclave sterilization. Thereby, the water-proof cap 33 is perfectly attached to the endoscope connector part 10, so that the convex part 72 of the water-proof cap 33 engages with the concave part 71 of the endoscope connector part 10.

Figure 7B:
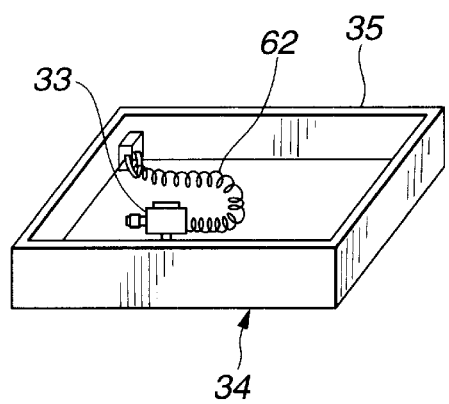

Also as FIG. 7B shows, the water-proof cap 33 for high temperature autoclave sterilization is connected to the tray 35 of the housing case 34 for sterilization by the chain 62, for example.

In the case of the water-proof cap 33a not suitable for high temperature autoclave sterilization where the convex part 72 is not created, the water-proof cap 33a can be attached to the electric connector part 11 of the endoscope connector part 10, although this is not shown. In the case of the present invention, however, the water-proof cap 33 supporting high temperature autoclave sterilization is connected to the tray 35 of the housing case 34 for sterilization, which is used for high temperature autoclave sterilization, so it is obvious when the water-proof cap 33a is attached by mistake to the endoscope 70 suitable for high temperature autoclave sterilization.

Also, the concave part 71 is not created in the electric connector 11 of the endoscope connector part 10 of the endoscopes 2a and 2b, which are not suitable for high temperature autoclave sterilization, so the water-proof cap 33 for high temperature autoclave sterilization cannot be perfectly attached. Therefore it can be identified that the endoscopes 2a and 2b are not suitable for high temperature autoclave sterilization.

As a result, the operator performing high temperature autoclave sterilization operation can inevitably identify whether the endoscope is suitable for high temperature autoclave sterilization.

(Sixth Embodiment)

The sixth embodiment of the present invention will now be described referring to FIG. 8.

In this embodiment, a housing case for sterilization, which is a kind of attaching element to allow attaching and housing only the endoscope 50 where the groove part 50a is created, described in the third embodiment, is in the configuration. The other configuration is the same as the third embodiment, where the same elements are denoted with the same numerals, for which description is omitted.

As FIG. 8 shows, the housing case for sterilization 80 of the present embodiment can house only the endoscope 50 where the groove part 50a shown in FIG. 5 is created.

In the tray 35 of the housing case for sterilization 80, the housing part 81, which is a concave part where the endoscope 50 and an instrument to be combined with the endoscope 50 can be housed, is created by the convex element 82 shown by shaded portions. Therefore the endoscope 50 and the instrument combined with the endoscope 50, which were used for the same patient, can be autoclaved at the same time. The operation part 8 and the insertion part 7 of the endoscope 50 can be disposed in predetermined positions of the housing part 81.

The tray 35 has a convex part 82a where the groove part 50a of the endoscope 50 is fit into. Since the groove part 50a is not created in the endoscopes 2a and 2b which are not suitable for high temperature autoclave sterilization, these endoscopes 2a and 2b cannot be set to the tray 35.

The water-proof cap 33 also has a concave part 83 so that the concave part 83 is combined with the convex part 84 created in the tray 35. Therefore the water-proof cap 33a, which does not have the concave part and is not suitable for high temperature autoclave sterilization, is not attached to the endoscope 50 which is suitable for high temperature autoclave sterilization.

In the fifth embodiment, where the water-proof cap 33 is connected to the tray 35, another water-proof cap must be attached at the cleaning operation before the sterilization process, but in the case of the sixth embodiment, the water-proof cap 33 attached at cleaning can be used as is during the high temperature autoclave sterilization process of the endoscope 50, unless a recognition error occurs.

In this way, the endoscopes 2a and 2b and a water-proof cap 33a which are not suitable for high temperature autoclave sterilization cannot be set to the tray 35 used for high temperature autoclave sterilization, so a recognition error, when the operator identifies the endoscopes 2a and 1b not suitable for the high temperature autoclave sterilization as the endoscope 50 suitable for high temperature autoclave sterilization, can be identified.

(Seventh Embodiment)

The seventh embodiment of the present invention will now be described referring to FIG. 9.

In the above embodiment, whether the endoscope is suitable for high temperature autoclave sterilization is identified by the structure, but in this embodiment, the monitor displays whether the endoscope is suitable for high temperature autoclave sterilization. The other configuration is the same as the above mentioned embodiments, where the same elements are denoted with the same numerals, for which description is omitted.

Figure 9A:
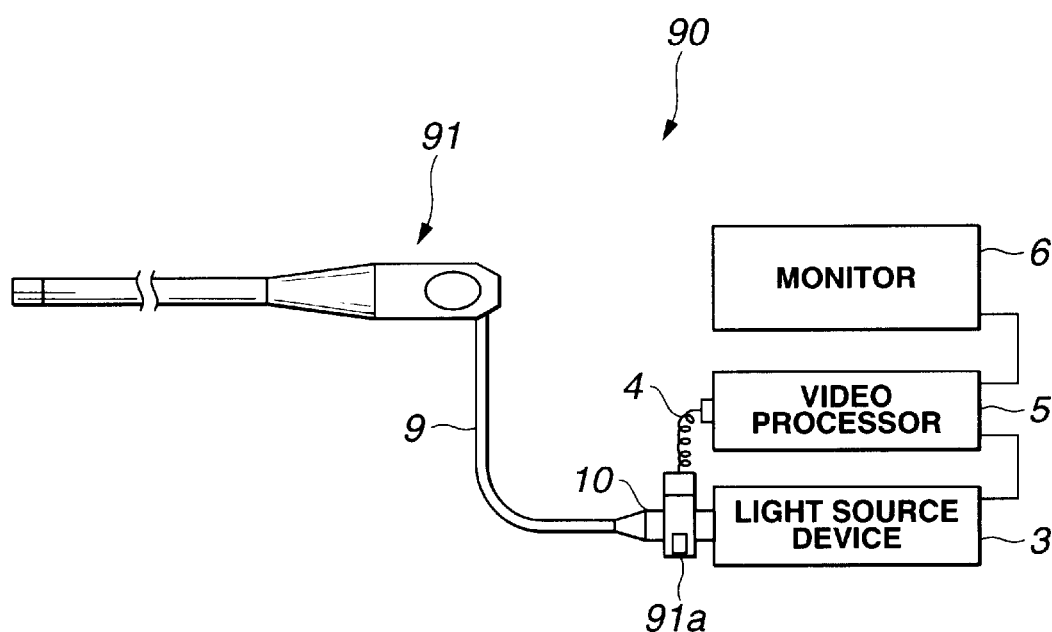
FIG. 9A and FIG. 9B are diagrams depicting the seventh embodiment of the present invention, where

As FIG. 9A shows, the endoscope device 90 of the present embodiment comprises an endoscope 91, the light source device 3, the video processor 5 and the monitor 6. The endoscope 91 has a recording part 91a where the endoscope information is recorded in the endoscope connector part 10. This recording part 91a may be disposed anywhere in the connector 10.

Figure 9B:
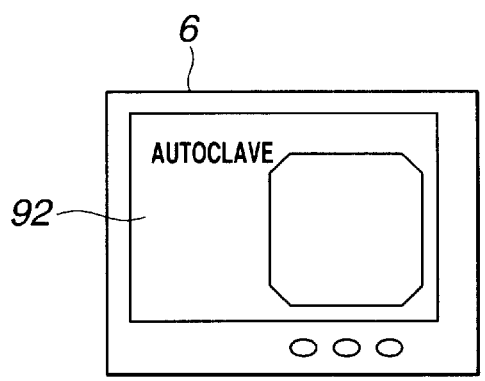

When the endoscope connector part 10 is connected to the video processor 5 via the signal cable 4, the endoscope information recorded in the recording part 91a is output to the video processor 5. The endoscope information output to the video processor 5 is displayed as characters, for example, "AUTOCLAVE" along with the endoscope image on the screen 92 of the monitor 6, as shown in FIG. 9B, by the signal processing superimposed on the endoscope screen. Thereby, the user knows that the endoscope 91 connected to the video processor 5 is suitable for high temperature autoclave sterilization.

The characters displayed on the screen 92 of the monitor 6 may indicate that the endoscope is not suitable for high temperature autoclave sterilization. Instead of displaying the characters, a notification tone may be output from the speaker of the monitor (not shown).

In this way, by creating a recording part where the endoscope information is recorded, whether the endoscope is suitable for high temperature autoclave sterilization can be identified using the characters displayed on the screen of the monitor or using a notification tone which is output.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. An endoscope system, comprising:
    an endoscope not suitable for high temperature autoclave sterilization, the endoscope being constituted such that it is provided with a predetermined inspection function and a predetermined appearance on the outer surface thereof and predetermined cleaning operations can be performed therein;
    an endoscope suitable for high temperature autoclave sterilization, the endoscope being constituted such that it is provided with a predetermined inspection function and a predetermined appearance on the outer surface thereof and predetermined cleaning operations can be performed thereon in a similar manner to the endoscope not suitable for high temperature autoclave sterilization; and
    an external endoscope device which is constituted such that these endoscopes can be connected thereto by an endoscope connector provided on each of the endoscope suitable for high temperature autoclave sterilization and the endoscope not suitable for high temperature autoclave sterilization,
    wherein the endoscope suitable for high temperature autoclave sterilization has a feature of the appearance on the outer surface of its corresponding endoscope connector which becomes an identification means for identifying that the endoscope is the one suitable for high temperature autoclave sterilization in addition to the appearance the endoscope not suitable for high temperature autoclave sterilization is provided on the outer surface thereof.

2. The endoscope system according to claim 1, wherein said identification means is a visual recognition means for recognizing whether said endoscope is suitable for high temperature autoclave sterilization by visual recognition.

3. The endoscope system according to claim 2, wherein said visual recognition means is an indication color placed at least on a part of the outer surface of the endoscope, and the endoscope suitable for high temperature autoclave sterilization and the endoscope not suitable for high temperature autoclave sterilization have different indication colors.

4. The endoscope system according to claim 3, wherein at least a part of the outer surface of said endoscope suitable for high temperature autoclave sterilization is a green color.

5. The endoscope system according to claim 2, wherein said visual recognition means is the external shape which appears on the outer surface of the endoscope, and the endoscope suitable for high temperature autoclave sterilization and the endoscope not suitable for high temperature autoclave sterilization have different external shapes.

6. The endoscope system according to claim 2, wherein said visual recognition means can be recognized from any circumference direction.

7. The endoscope system according to claim 1, wherein said identification means is a combining element required for cleaning, disinfecting or sterilizing at least the endoscope suitable for high temperature autoclave sterilization.

8. The endoscope system according to claim 7, wherein said combining element is a water-proof cap.

9. The endoscope system according to claim 1, wherein said identification means is a recording part disposed in said endoscope and where the endoscope information is recorded, and identifies whether said endoscope is suitable for high temperature autoclave sterilization by outputting the endoscope information recorded in this recording part to the external endoscope device.

10. The endoscope system according to claim 1, further comprising a body contacting instrument which contacts the bodily fluid of a patient and is suitable for high temperature autoclave sterilization and a body contacting instrument which contacts the bodily fluid of a patient and is not suitable for high temperature autoclave sterilization, wherein said body contacting instrument is provided with the identification means for identifying whether the body contacting instrument is suitable for high temperature autoclave sterilization similar to said endoscope.

11. The endoscope system according to claim 10, wherein said body contacting instrument suitable for high temperature autoclave sterilization and said endoscope suitable for high temperature autoclave sterilization are housed in a same housing case for sterilization.

12. An endoscope system comprising:
    an endoscope suitable for high temperature autoclave sterilization;
    an endoscope not suitable for high temperature autoclave sterilization;
    an external endoscope device to which these endoscopes are connected; and
    an identification means for identifying whether the endoscope is suitable for high temperature autoclave sterilization;
    wherein said identification means identifies whether said endoscope is suitable for high temperature autoclave sterilization by the difference in structure of attaching elements which are constructed such that each of said attaching elements can be attached only to one endoscope.

13. The endoscope system according to claim 12, wherein said attaching element is a housing case for sterilization where said endoscope suitable for high temperature autoclave sterilization is housed.

14. The endoscope system according to claim 12, wherein said attaching element is a water-proof cap.

15. An endoscope system comprising:
    an endoscope suitable for high temperature autoclave sterilization;
    an endoscope not suitable for high temperature autoclave sterilization;
    an external endoscope device to which these endoscopes are connected; and
    an identification means for identifying whether the endoscope is suitable for high temperature autoclave sterilization;
    wherein said identification means is an attaching element connected to the endoscope suitable for high temperature autoclave sterilization, and identifies whether said endoscope is suitable for high temperature autoclave sterilization depending on whether said attaching element is connected to the endoscope.

16. An endoscope system, comprising:

an endoscope not suitable for high temperature autoclave sterilization, the endoscope being constituted such that it is provided with a predetermined inspection function and a predetermined appearance on the outer surface thereof and predetermined cleaning operations can be performed therein;

an endoscope suitable for high temperature autoclave sterilization, the endoscope being constituted such that it is provided with a predetermined inspection function and a predetermined appearance on the outer surface thereof and predetermined cleaning operations can be performed thereon in a similar manner to the endoscope not suitable for high temperature autoclave sterilization; and an external endoscope device which is constituted such that these endoscopes can be connected thereto, wherein the endoscope suitable for high temperature autoclave sterilization has a feature of the appearance on the outer surface thereof which becomes an identification means for identifying whether the endoscope is the one suitable for high temperature autoclave sterilization or the one not suitable for high temperature autoclave sterilization in addition to the appearance the endoscope not suitable for high temperature autoclave sterilization is provided on the outer surface thereof, wherein said identification means is a visual recognition means for recognizing whether said endoscope is suitable for high temperature autoclave sterilization by visual recognition, and wherein said visual recognition means is the external shape which appears on the outer surface of the endoscope, and the endoscope suitable for high temperature autoclave sterilization and the endoscope not suitable for high temperature autoclave sterilization have different external shapes.

17. An endoscope system, comprising:

an endoscope not suitable for high temperature autoclave sterilization, the endoscope being constituted such that it is provided with a predetermined inspection function and a predetermined appearance on the outer surface thereof and predetermined cleaning operations can be performed therein;

an endoscope suitable for high temperature autoclave sterilization, the endoscope being constituted such that it is provided with a predetermined inspection function and a predetermined appearance on the outer surface thereof and predetermined cleaning operations can be performed thereon in a similar manner to the endoscope not suitable for high temperature autoclave sterilization; and an external endoscope device which is constituted such that these endoscopes can be connected thereto, wherein the endoscope suitable for high temperature autoclave sterilization has a feature of the appearance on the outer surface thereof which becomes an identification means for identifying whether the endoscope is the one suitable for high temperature autoclave sterilization or the one not suitable for high temperature autoclave sterilization in addition to the appearance the endoscope not suitable for high temperature autoclave sterilization is provided on the outer surface thereof, and wherein said identification means is a combining element required for cleaning, disinfecting or sterilizing at least the endoscope suitable for high temperature autoclave sterilization.

\* \* \* \* \*